United States Patent [19]

Brown

[11] Patent Number: 5,149,627

[45] Date of Patent: Sep. 22, 1992

[54] IMMUNOASSAY FOR CELL PROTEINS

[75] Inventor: James E. Brown, Lafayette, Calif.

[73] Assignee: Miles, Inc., Elkhart, Ind.

[21] Appl. No.: 823,581

[22] Filed: Jan. 21, 1992

Related U.S. Application Data

[63] Continuation of Ser. No. 299,385, Jan. 23, 1989, abandoned.

[51] Int. Cl.$^5$ ............................................. G01N 33/53
[52] U.S. Cl. .................................. 435/7.1; 435/7.21; 435/7.2; 436/501; 530/387.1; 530/389.1; 530/388.25; 530/413; 935/102; 935/108
[58] Field of Search ...................... 435/7.1, 7.21, 7.23, 435/7.8; 436/501, 811; 530/387.1, 387.7, 387.25, 389.1; 935/102

[56] References Cited

PUBLICATIONS

Eaton et al., (1987) J. Biol. Chem., vol. 262, No. 7, pp. 3285-3290.
Goding, *Monoclonal Antibodies, Principles and Practice*, Academic Press, Inc., 1983, Chapter 8, pp. 250-261.

*Primary Examiner*—Margaret Moskowitz
*Assistant Examiner*—Ardin H. Marschel
*Attorney, Agent, or Firm*—Elizabeth F. Enayati; David J. Aston; James A. Giblin

[57] ABSTRACT

An immunoassay for cellular proteins which may be present as contaminants in a product purified from mammalian cell culture. Since mammalian cell culture requires the use of protein-containing media, the assay must be specific in recognizing cellular proteins but not media proteins. This is accomplished by selective adsorption of an antiserum to cellular proteins against media proteins. Quantification of the assay may be improved through the use of a purified antigen, namely fibronectin, which is known to be highly immunogenic.

3 Claims, 4 Drawing Sheets

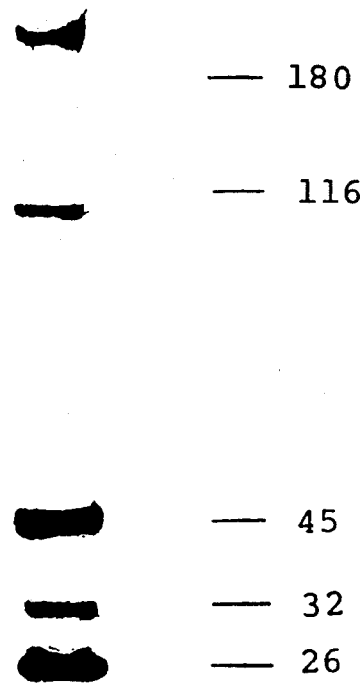
FIG._1

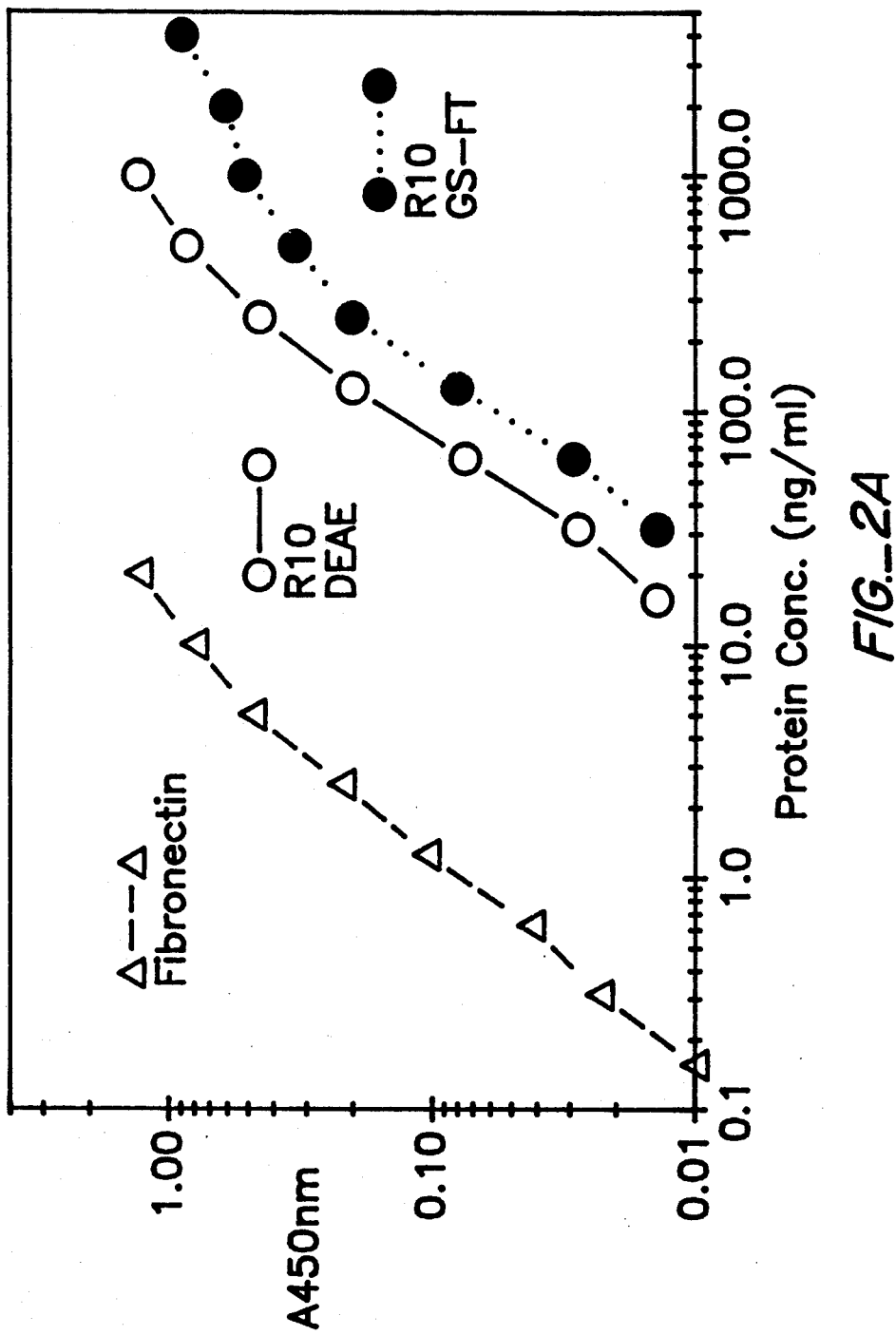

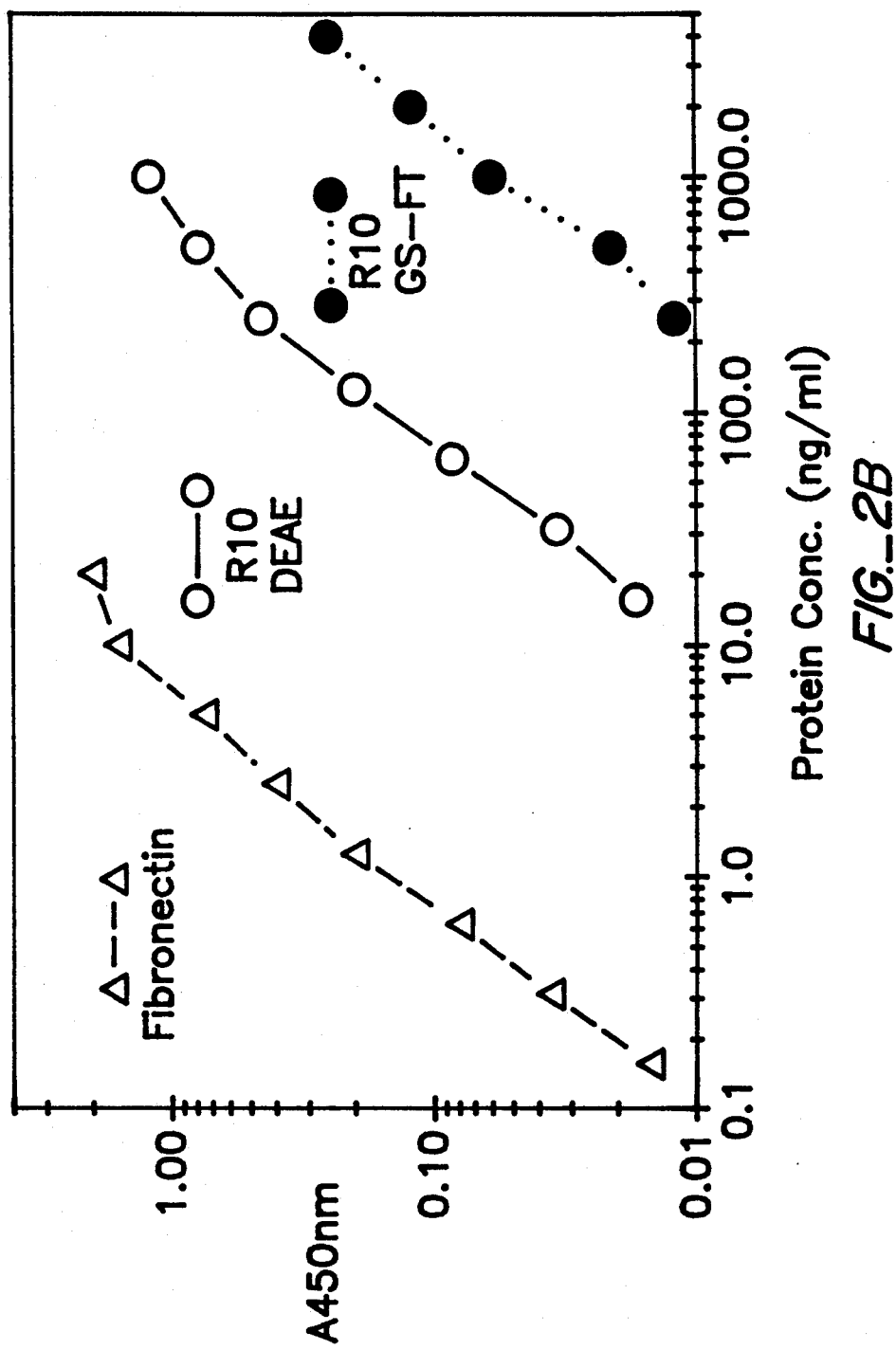
FIG._2B

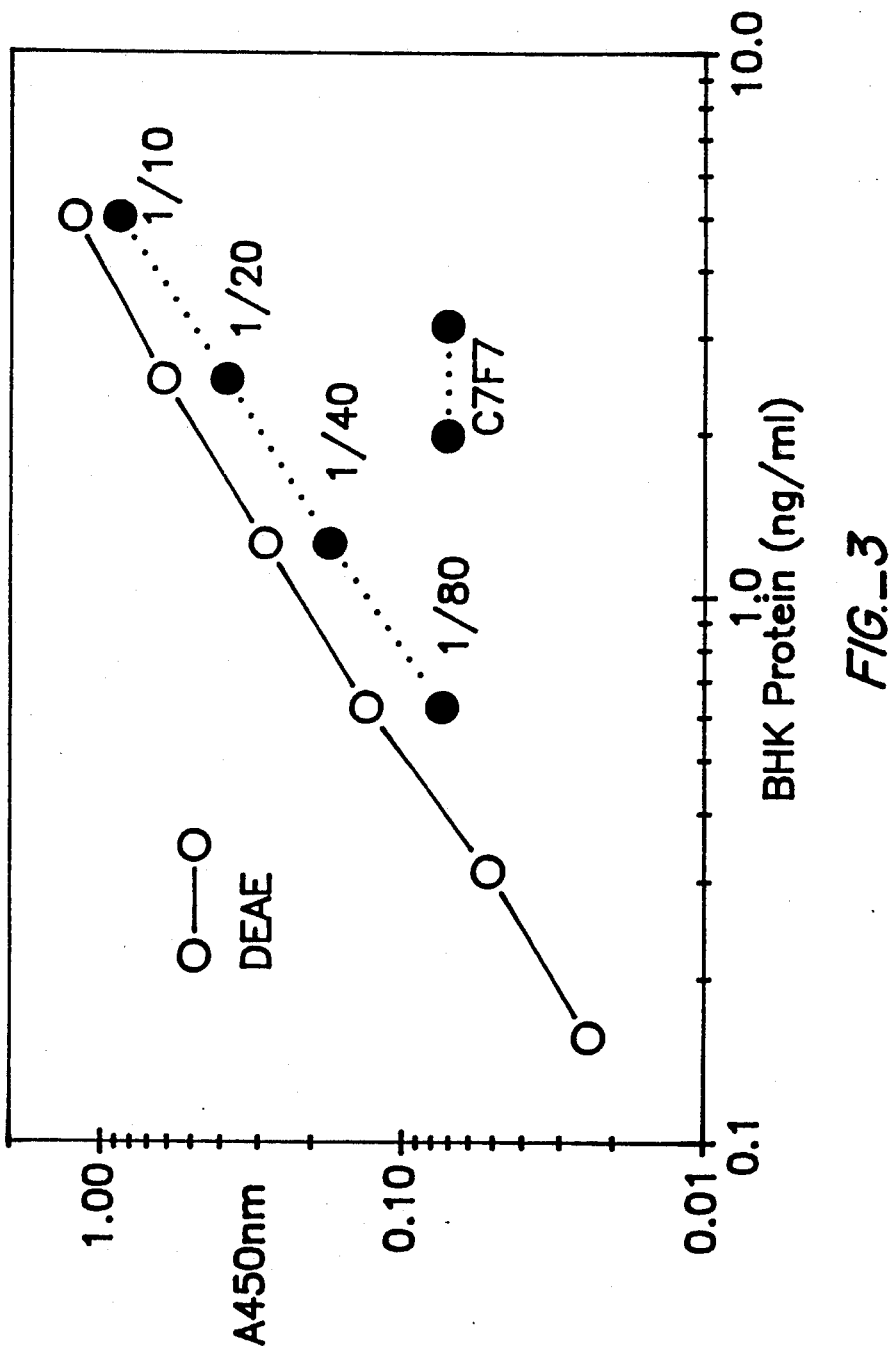
FIG._3

IMMUNOASSAY FOR CELL PROTEINS

This application is a continuation of co-pending application Ser. No. 07/299,385, filed on Jan. 23, 1989, now abandoned.

BACKGROUND OF THE INVENTION

1. Field of the Invention

The present invention relates generally to the field of immunoassays, and more particularly to an immunoassay intended to measure the cellular proteins from a host cell grown in cell culture. The host cell will generally have been used to produce a protein which has been isolated and purified for therapeutic use. The therapeutic protein will generally have been engineered into the host cell by recombinant DNA techniques.

2. Description of the Related Art

Immunoassays are generally known in the art. These assays use an antibody or antibodies to measure the amount of a given antigen in a sample. A typical immunoassay format, known generally as a sandwich ELISA (enzyme-linked immunosorbent assay), uses an enzyme-linked antibody for detection purposes. In one format, this detection antibody binds to an antigen to be assayed. First a "capture" antibody is immobilized, such as by coating it onto the well of a plastic plate. A sample containing an unknown amount of antigen is then applied. The antigen is captured by the antibody on the plate. The plate is washed free of other proteins and other materials. Then, the detection antibody is applied, and it binds to the antigen captured by the capture antibody. This detection antibody has been coupled to a chemical marker, typically an enzyme, which gives off a color when reacted with a substrate. Alternatively the detection antibody can be coupled with biotin, and the antibody detected using enzyme-conjugated streptavidin or avidin. The amount of detection antibody bound to the complex is then determined colorimetrically.

This format of ELISA is termed a "sandwich" ELISA, in that the antigen is akin to a slice of meat between two slices of antibody bread. An assay in this format usually uses the same polyclonal antisera for the capture antibody and the detection antibody. Monoclonal antibodies are only used for both capture and detection antibodies when they have been found to be reactive with different sites on the antigen.

A review of various enzyme immunoassays is contained in Kurstak, "Progress in Enzyme Immunoassays, Experimental Design, and Interpretation," Bull. W.H.O. 63(4):793-811 (1985). Because of its description of various immunoassay formats which may be used in connection with the present invention, this disclosure is hereby incorporated by reference into the present specification. A specific example of an immunoassay used in the production of a recombinant DNA product is found in Ferrua et al., "Human Interleukin 2 Detection at the Picomolar Level by Sandwich Enzyme Immunoassay," J. Immunol. Methods, 97:215-220 (1987).

Anicetti et al., "Immunoassay for the Detection of E. Coli Proteins in Recombinant DNA Derived Human Growth Hormone," J. Immunol. Methods, 91:213-224 (1986), describe an ELISA test for the quantitative measurement of E. coli host cell proteins in recombinant human growth hormone. This is a multiple antigen immunoassay using affinity purified polyclonal antibodies. Because E. coli is not grown in media containing proteins and is processed from a cell paste, there is no suggestion in this article that one should or could deplete the antibody of anti-media antibodies. In the series of experiments described in this reference, the antiserum is purified by passing it over a chromatography column containing reference E. coli proteins. Only the antibodies which bound to the immobilized E. coli proteins were used in the assay.

Lucas et al., "Enzyme-linked immunosorbent assays (ELISAs) for the determination of contaminants resulting from the immunoaffinity purification of recombinant proteins," J. Immunol. Methods, 13:113-122 (1988) disclose ELISA's for the determination of contaminating proteins in rDNA and monoclonal antibody products produced in mammalian cell culture. However, these assays are direct assays for one particular contaminating protein, e.g. the bovine IgG contained in fetal bovine serum. A specific antibody to this IgG is used.

Depleted antisera have been previously used in certain test procedures. Lundblad et al., "The Antigenic Nature of Heat Treated Human Plasma Proteins," Vox. Sang. 5:122-137 (1960) describe in a general sense the use of a depleted antiserum to evaluate the presence or absence of a particular antigen in an Ouchterlony assay.

J. C. Giddings, "The Purification of Factors VIII and IX, and Production of Specific Antisera," Vol. 5 Ch. 4, Methods in Haematology, 1982, discloses absorption of antisera to F.VIII:RAg with F.VIII:RAg-deficient plasma. This was to produce an antiserum specific to F.VIII:RAg.

Other assays have previously employed depleted anisera. See, e.g. Venn et al., "Limitations of a hemolytic plague assay for IgG-anti-IgG rheumatoid factor-producing cells." J. Immunol. Methods 102:195-204 1987.

SUMMARY OF THE INVENTION

The present invention measures host cell proteins which may be contaminating a product produced in mammalian cell culture. Mammalian cell culture requires the use of media containing proteins, such as fetal bovine serum, or as practiced in connection with the present invention, media containing human proteins such as human serum albumin. In particular, mammalian host cells such as Baby Hamster Kidney (BHK) cells must be grown in media containing human or animal plasma proteins.

Mammalian host cell proteins are used to immunize an animal to produce an antiserum which may be used in an immunoassay for host cell proteins which may be contaminating the desired product. This antiserum will necessarily also contain antibodies to media proteins. These media proteins are highly immunogenic in animals, but, in the case of human media proteins, not immunogenic in humans. Therefore, measurement of these human media proteins is neither necessary nor desirable in an assay of contaminating host cell proteins.

The present invention provides an assay for host cell proteins which is quantitative and which does not measure media proteins. This is accomplished by depleting the antiserum raised to both the host cell proteins and the media proteins by adsorbing it with immobilized media proteins, thereby depleting the antiserum of antibodies to media proteins. This antiserum is then used in a sandwich ELISA. Because the antiserum is polyclonal and the antigen mixture is complex, the same antiserum is used as a capture antibody and a detection antibody.

In the process of the present invention, host cell proteins are first partially purified away from the media proteins. Then, antiserum is raised to this preparation, using standard techniques, in rabbits. The antiserum is immunopurified by passage over a column containing the immobilized immunizing antigens. Then, this antiserum is depleted by passing it over media proteins which have not been used to grow cells and therefore contain no cell proteins. This depleted antiserum is then used to quantify host cell proteins. An important part of the quantification process is the recognition that certain host cell proteins may be more immunogenic than others and therefore their titer in the antiserum is not truly representative of their presence in host cell protein which may contaminate a product preparation.

For example, fibronectin may make up only a small fraction of the measured host cell protein. Yet, antisera to host cell protein may contain a high titer of antibodies to this protein. In that case, a highly purified preparation which contained a small amount of host cell protein and in which a small proportion of that host cell protein was fibronectin would appear to have much more total host cell protein due to the strong immunoreactivity of the fibronectin. The present invention further provides a means for correcting for this effect.

BRIEF DESCRIPTION OF THE DRAWINGS

FIG. 1 is a Western blot showing a partially purified mixture of host cell proteins and media proteins blotted with anti-host cell protein antibodies;

FIG. 2A is a graph showing binding of fibronectin and host cell protein to anti-BHK antibodies; and FIG. 2B is a graph showing binding of fibronectin and host cell protein to anti-fibronectin antibody; and FIG. 3 is a graph showing host cell protein dose response at two different stages of the purification process.

DESCRIPTION OF THE PREFERRED EMBODIMENT

The preferred embodiment of the present invention utilizes Baby Hamster Kidney (BHK-21) cells which have been transfected with the gene for Factor VIII, as described in Nature 312:326-330 (1984).

EXAMPLE 1

Preparation of DEAE Eluate Antigen

Cells which have been selected for use in large scale production of recombinant Factor VIII (rFVIII) were selected from the master cell bank which was established according to the applicable Office of Biologics Points to Consider. The cells were expanded from a frozen ampule in media containing Dulbecco Modified Eagle and Ham F12 basal media supplemented with 7.5% dialyzed fetal bovine serum (FBS) and 10uM methotrexate. After 2 weeks, or 3-4 passages, the cells were transferred to growth media for 3-4 days (1 passage). This media contained DM/F12 with 7% FBS. The cells were then transferred to media containing 4 g/L plasma protein fraction (Cutter Plasmanate ®), 5 mg/L insulin and 2.5 mg/L transferrin. Harvests from roller bottles were taken at 48 hr. intervals.

Four harvests were individually partially purified (to a DEAE eluate stage) as described by Eaton et al. J. Biol. Chem. 262 3285-3290 (1987).

EXAMPLE 2

Preparation of Immunopurified Antiserum

Twelve rabbits (3 rabbits from each of 4 roller bottle produced harvests) were immunized with the DEAE eluates (from Example 1, with elution buffer 0.01,M $CaCl_2$, 5% glycerol, 0.02M imidazole, 0.25M NaCl, pH 7.0). The initial injection took place with 100 μg of protein (based on $A_{280}$ using 1% E $A_{280}=10.0$) in Freund's complete adjuvant. Boosts also took place at weekly intervals for 5 weeks with a bleed on the 6th and subsequent weeks.

These harvests were taken at 48 hr. intervals. Since a 4th harvest from production run (PR) 22 produced a very low level of factor VIII, a 4th harvest from an earlier run PR 17 was used. The factor VIII levels, protein by $A_{280}$ and level of hamster fibronectin (see later for assay method) on each harvest is reported in Table 1, below:

TABLE 1

| DEAE Eluate | Factor VIII level | $A_{280nm}$ | μg/ml Hamster Fibronectin | Number Immunized Rabbits |
|---|---|---|---|---|
| PR 22 $H_1$ | 24.4 u/ml | 1.72 | 4.9 | 3 |
| PR 22 $H_2$ | 27.6 u/ml | 1.22 | 6.6 | 3 |
| PR 22 $H_3$ | 16.0 u/ml | 1.17 | 21.2 | 3 |
| PR 17 $H_4$ | 23.2 u/ml | 1.32 | 43.6 | 3 |

Antiserum was then harvested from the rabbits as follows: Equal volumes of rabbit serum from each of the 12 rabbits was collected, pooled and precipitated with caprylic acid according to the method of McKinney and Parkinson, J. Immunol. Methods, 96:271-278 (1987). This material was further purified by 45% ammonium sulfate precipitation, dialyzed into 0.05M Tris, 0.05M NaCl, 0.02% $NaN_3$ and applied to a resin of controlled pore glass (Sigma CPG) to which the proteins present in the DEAE eluates shown in Table 1 were coupled. The proteins present in an equal volume pool of the 4 harvests above were coupled by the method of S. K. Roy, D. V. Weber and W. C. McGregor, J. Chromatography 303:225-228, 1984. A column of 12 mL with 4.15 mg of protein ($A_{280}$ units) per mL of resin was used to immunopurify the antibodies. Elution of antibodies (which bound to the immobilized DEAE eluate proteins) took place with 0.25M glycine-HCl, pH=2.9, with neutralization of the pH by collection into 1/10th volume of 1M pH 8.5 Tris buffer.

EXAMPLE 3

Depletion of Purified Antiserum

As it was necessary to deplete the antibodies of reactivity toward media proteins and Factor VIII, a depletion resin (CPG) was prepared by coupling the proteins present in an eluate prepared from production media as a DEAE eluate 149.6 $A_{280}$ units, 16 g CPG, 7.2 mg/mL coupled (18 mL resin) —92.8% efficient coupling, and a DEAE eluate from Koate ® AHF concentrate powder 4.7 mg/mL, 3 mL column, 96.3% efficient coupling. The production media had not been used for cell culture and was according to the formulation given in Example 1.

These DEAE eluates were prepared according to the method described in Example 1. The combined resins were mixed and packed into a single column of 21 mL containing 130 $A_{280}$ units of media proteins and 14 $A_{280}$ units of plasma-derived factor VIII, both as DEAE eluates, i.e. partially purified.

The immunopurified antisera from Example 2 was passed over the depletion resin in passes of 10 mg of IgG per pass, then pooled and concentrated and repassed for a total of 4 passes.

To measure the depletion of Factor VIII, antisera was coated at 1 μg/ml (100 μl) to each well of a NUNC microtiter plate at different stages of depletion by dilution into PBS/KCl buffer (8g NaCl, 1.05 g Na$_2$HPO$_4$, 0.2 g NaH$_2$PO$_4$, 0.2 g KCl, per liter, pH=7.3). Following washing, a preparation of immunopurified rFVIII (see D. L. Eaton et al. J. Biol. Chem. 262: 3285-3290, 1987) (100 ul) was then added to the microtiter well (buffer 0.02M Tris.HCl, 0.5 m NaCl, 0.5% Tween 20, detergent 0.01% thimerosal, pH=8.0). Detection of antibody bound Factor VIII was by C7F7 a monoclonal antibody to the light chain of Factor VIII:C (*Nature*, Supra) that was conjugated with horseradish peroxidase with 3, 3' tetramethyl benzidine as substrate.

That antibody to Factor VIII:C has been raised and then removed is demonstrated in Table 2 below:

TABLE 2

| Conc. rFVIII #3390-47-4 units/mL | IAP | A$_{450}$ values/20 min. | | |
|---|---|---|---|---|
| | | 1st Depletion | 2nd Depletion | 3rd Depletion |
| 2.5 | 1.203 | 0.276 | 0.242 | 0.175 |
| 1.25 | 0.682 | 0.147 | 0.141 | 0.087 |
| 0.61 | 0.389 | 0.095 | 0.079 | 0.045 |
| 0.31 | 0.220 | 0.049 | 0.036 | 0.021 |

Each row of data in Table 2 indicates a different dilution of the immunoaffinity purified antiserum (IAP). The first column refers to units of F.VIII activity in the starting material. Values in other columns, headed "A$_{450}$ values/20 min" represent the amounts of IAP-bound rFVIII detected by C7F7. Successive depletions therefore show decreases in anti Factor VIII concentration in the antiserum. F.VIII is not detected by the depleted IAP itself in the host cell protein immunoassay.

EXAMPLE 4

Presence of Fibronectin

The following shows how fibronectin was demonstrated to be present in the pooled DEAE eluates used as an assay standard.

BHK cells in culture are known to secrete fibronectin (Sekiguchi, K., Fukuda, M. and Hakomori, S., J. Biol. Chem. 256: 6452-6462, (1981)). When the DEAE eluates used to immunize rabbits in Example 2 above were examined by Western blot analysis in a reduced gel (SDS/PAGE), a major band was seen at approximately 200 Kd A media protein control processed as, DEAE eluate showed no such band. Passage over gelatin-Sepharose removed this band as visualized in gels and blots (data not shown).

Gelation-Sepharose chromatography has been used to purify BHK cellular fibronectin—see Sekiguchi et al. From the foregoing, it is concluded that hamster fibronectin is present in the DEAE eluates from the cell culture fluid.

FIG. 1 shows a Western blot analysis carried out according to the technique of Pluskal et al., Biotechniques, 4:272-283 (1986). An intermediate purity DEAE eluate pool, lane 1 and a medium control, lane 2, were run with 5 micrograms total protein per lane. The gel was blotted with immunopurified and anti-media reactivity depleted anti-BHK protein antibodies, such as prepared in Example 3. No bands are visible in the medium control lane. The band at Mr approximately 200 kd is seen to increase with successive harvests (data not shown).

EXAMPLE 5

Quantification of Assay

The following example shows how a standard was assigned for quantifying BHK protein in the assay. First, purified hamster fibronectin prepared by the gelatin-Sepharose method of Sekiguchi et al. (supra) was shown to give a strong signal in the BHK protein ELISA. Fibronectin was purified from rFVIII-transfected cells grown essentially as described in Example 1, but adapted to suspension culture. Cellular protein was isolated by two gelatin-Sepharose chromatography steps. Antibodies were raised using 50 μg of this purified fibronectin as an immunizing agent as described in Example 2. These antibodies were used to develop a quantitative hamster fibronectin ELISA.

FIG. 2B shows the dose-response curves in the hamster fibronectin ELISA. Both purified hamster fibronectin and a mixture of BHK proteins/media proteins as described earlier (i.e. DEAE eluate) were assayed at different protein concentrations, with protein concentration (horizontal axis) determined by a Bradford protein assay. A$_{450}$ values represent the ELISA signal. By passage through a gelatin-Sepharose column (R10 GS-FT) the signal is decreased by 96.5% indicating removal of a substantial amount of fibronectin. This is indicated by the displacement of the solid circles relative to the open circles. FIG. 2A similarly shows the dose-response curves in the BHK protein ELISA. Purified fibronectin binds to this population of BHK protein antibodies with a very similar dose-response to that seen in FIG. 2A with antibody specific to hamster fibronectin. The preparation of BHK/media proteins (R10 DEAE) also binds similarly to that seen to hamster fibronectin antibody, however removal of fibronectin by passage over a gelatin-Sepharose column, decreases the signal, but by only 59.7% instead of the 96.5% in the fibronectin ELISA. This indicates that other antigens are being measured in the BHK protein ELISA in addition to fibronectin.

The protein elution profile (by A$_{280}$) for this mixture of BHK/media proteins (R10 DEAE eluate) from the gelatin-Sepharose column resulted in a single peak around fraction 3. The 4M urea eluate peak was shown to contain pure hamster fibronectin (media proteins show no binding to this column). This peak constituted 2% of the total protein (multiple experiment average, by A$_{280}$) present in this pooled antigen mixture. 75% of the BHK protein ELISA activity was found in this peak, however. Since 75% of the ELISA activity is accounted for by 2% of the protein, a concentration of total BHK protein in the assay standard was determined to be 28.3 μg/mL. For example, if 1 06 mg/mL = total protein concentration in standard
2% = amount of fibronectin present in standard; and
75% = % of assay signal attributable to fibronectin,
then 1.06 mg/mL X.020÷0.75=28.3 μg/mL. This concept assumes that the 25% of the activity that is non-fibronectin gives a proportional signal by ELISA.

EXAMPLE 6

Use of Assay

This example illustrates monitoring cellular protein impurities at various steps in product purification. Data are shown in Table 3 for BHK protein at three different steps during the purification of factor VIII.

TABLE 3

| Process Step | BHK Protein (ng/ml) Run No.: | | |
|---|---|---|---|
| | 1 | 2 | 3 |
| (1) DEAE | 4200 | 3342 | 2940 |
| (2) C7F7 | 1.6 | 2 | 2.3 |
| (3) UF/DF Pool | 0.52 | 1 | 0.63 |

BHK values are given in ng/mL. Table 3 shows the reduction in BHK protein across three successive, selected (arbitrarily chosen) steps in the purification process.

Another preparation of Factor VIII (see FIG. 3) showed that following various purification steps, a parallel dose response curve is exhibited. This indicates that the non-fibronectin contaminants respond in the ELISA in a similar manner to fibronectin. The data points on the two curves in FIG. 3 were obtained by dilution of samples: The C7F7 material was also depleted of fibronectin by passage over gelatin Sepharose.

The Foregoing Examples describe the presently preferred embodiment of the present invention. This embodiment relates to the detection of BHK proteins in a mammalian cell culture of BHK cells transfected with the Factor VIII gene, said culture being carried out in media containing Plasmanate ® as the principle media protein. Plasmanate ® is derived from human plasma Fraction V and contains about 85% normal serum albumin. Numerous variations are possible within the scope of the present invention. Many other cell lines transfected with many possible genes coding for desired products can be grown in numerous media formulations. Various immunoassay formats may be used. Various "markers," such as biotin and horseradish peroxidase may be linked to detection antibodies.

Therefore the scope of the present invention should not be interpreted as limited to the particular embodiments described above, but rather by the following claims.

What is claimed is:

1. A method of determining the amount of cellular proteins in a therapeutic protein preparation expressed from mammalian cells that have been grown in the presence of media proteins, the method consisting of the sequential steps of
   (a) obtaining a partially purified sample that includes both cellular proteins from the mammalian cells and media proteins in which the cells were grown;
   (b) using the sample to prepare antiserum which includes polyclonal antibodies to both the cellular proteins and the media proteins;
   (c) immunopurifying the antiserum of step (b) by contacting the antiserum of step (b) with immobilized immunizing antigens;
   (d) contacting the antiserum of step (c) with immobilized media proteins under conditions sufficient to remove the antibodies to media proteins from the antiserum, thereby producing an antiserum depleted of antibodies to the media protein; and
   (e) using the depleted antiserum of step (d) in an immunoassay to determine the amount of cellular proteins in the therapeutic protein preparation.

2. The method of claim 1 wherein one of the cellular proteins in fibronectin.

3. The method of claim 1 wherein the immunoassay of step (e) is an ELISA.

* * * * *